United States Patent
Maarse

Patent Number: 6,128,535
Date of Patent: Oct. 3, 2000

[54] AUTOMATIC CAPTURE VERIFICATION IN MULTISITE CARDIAC PACING

[75] Inventor: Albert Maarse, Amstelveen, Netherlands

[73] Assignee: Cardiac Pacemakers, Inc., St. Paul, Minn.

[21] Appl. No.: 08/986,319

[22] Filed: Dec. 5, 1997

[51] Int. Cl.[7] ................................. A61N 1/37
[52] U.S. Cl. ............................................. 607/28
[58] Field of Search ............................ 607/27, 28

[56] References Cited

U.S. PATENT DOCUMENTS

| | | | |
|---|---|---|---|
| 3,757,792 | 9/1973 | Mulier et al. | 128/419 P |
| 3,920,024 | 11/1975 | Bowers | 128/419 PG |
| 3,949,758 | 4/1976 | Jirak | 128/419 PG |
| 4,055,189 | 10/1977 | Auerbach et al. | 128/419 PG |
| 4,114,627 | 9/1978 | Lewyn et al. | 128/419 PT |
| 4,228,803 | 10/1980 | Rickards | 128/419 PG |
| 4,305,396 | 12/1981 | Wittkampf et al. | 128/419 PG |
| 4,686,988 | 8/1987 | Sholder | 607/28 |
| 4,708,142 | 11/1987 | DeCote, Jr. | 128/419 PT |
| 4,762,136 | 8/1988 | Baker, Jr. | 128/786 |
| 4,955,376 | 9/1990 | Callaghan et al. | 128/419 PG |
| 4,969,460 | 11/1990 | Callaghan et al. | 128/419 PG |
| 5,222,493 | 6/1993 | Sholder | 128/419 P |
| 5,324,310 | 6/1994 | Greeninger et al. | 607/28 |
| 5,331,966 | 7/1994 | Bennett et al. | 128/696 |
| 5,431,693 | 7/1995 | Schroeppel | 607/28 |
| 5,601,615 | 2/1997 | Markowitz et al. | 607/28 |

*Primary Examiner*—William E. Kamm
*Attorney, Agent, or Firm*—Nikolai, Mersereau & Dietz, P.A.

[57] ABSTRACT

An implantable device and method of cardiac stimulation that automatically verifies capture and a threshold effectiveness of stimulation of a cardiac stimulator. During predetermined periods, the device utilizes 2 or more pacing/sensing electrodes positioned within an electrically continuous area of the heart, wherein one electrode is used to provide a pacing stimulus while the other electrode or electrodes are used to verify capture or a threshold effective strength. A predetermined blanking period is provided to avoid detection of the electrical stimulus transmitted to one electrode from a pulse generator. After expiration of the predetermined blanking period the remaining electrodes detect depolarization of the surrounding tissue.

11 Claims, 5 Drawing Sheets

AUTOMATIC CAPTURE VERIFICATION IN MULTISITE CARDIAC PACING

BACKGROUND OF THE INVENTION

I. Field of the Invention

This invention relates generally to an implantable cardiac stimulating device and more particularly relates to a cardiac stimulating device capable of using multiple electrodes for automatic capture and threshold verification. Each of several electrodes are utilized for sensing, pacing and capture verification within an electrically continuous area of the cardiac muscle. During predetermined periods, the stimulation device verifies the effectiveness of a stimulation impulse by applying the stimulation impulse to the heart muscle via one electrode and then the electrical signal resulting from the induced cardiac muscle activity is evaluated by one or more of the other electrodes.

II. Discussion of the Related Art

Cardiac stimulators typically include a pulse generator, limited power supply, electrical leads, and an integrated circuit or microprocessor based controller. In order to maximize use of the limited power supply, it is desirable to set the lowest output energy that reliably causes depolarization of the corresponding cardiac muscle resulting from an electrical stimulus generated by the pulse generator. To ensure the reliability of pacing, it is common practice to determine the minimum output energy that induces a cardiac depolarization ("the energy threshold") manually during patient follow-ups, and then set the pacemaker's output at this minimum setting plus a wide error margin, usually double or triple the minimum effective energy. This error margin is meant to account for the changes in energy requirement that may occur over the time between the patient follow-ups. It is far more economic if the pacemaker can track the changes of the minimum required energy, and adjust its output energy settings to that, with a much smaller error margin. In order to do so, it is necessary that the pacemaker is able to verify if an electrical stimulus is effective. This automatic verification is known as auto capture.

Over the years single or dual chamber cardiac pacers have evolved, whereby capture verification and threshold are automatically determined. The dual chamber cardiac pacers may be programmed such that sensing occurs in one chamber of the heart and pacing is directed to another chamber of the heart. The sensing amplifiers of such devices generally have a refractory period of sufficient length to mask the initial responses of the heart to the stimulation pulses or stimulated heartbeats. This refractory period is necessary to block out artifacts caused by polarization of the electrodes coupled to the lead which act as both pacing and sensing electrodes.

Mulier, in U.S. Pat. No. 3,757,792 describes a pacemaker coupled to two leads each having an electrode. One of the electrodes is designated for normal pacing and sensing and the other electrode is dedicated to sensing of heartbeats that are induced by the other electrode, wherein both electrodes are situated on the ventricles. Each electrode of the Mulier device is limited to a specific task, one for stimulating and the other for detecting. The present invention recognizes the advantages to including multiple pacing electrodes, wherein the capture of each electrode's stimulus may be verified by the other electrode(s). Hence, electrodes capable of functioning both for stimulation and detection are desirable.

Other cardiac pacing devices have been described that verify the effectiveness of a stimulus from one electrode using the same electrode for verification. When using a single electrode for verifying the effectiveness of its own stimulus, various techniques are required to minimize detection of the polarization built up on the pacing electrode or alternatively, the device must use T-wave secondary heart beat characteristics. Representative of such devices are, for example, those disclosed by Bowers, U.S. Pat. No. 3,920,024; Jirak, U.S. Pat. No. 3,949,758; Auerbach et al., U.S. Pat. No. 4,055,189; Lewyn et al., U.S. Pat. No. 4,114,627; Rickards, U.S. Pat. No. 4,228,803; Wittkampf et al., U.S. Pat. No. 4,305,396; Decote, Jr. U.S. Pat. No. 4,708,142; and Callaghan et al., U.S. Pat. Nos. 4,955,376 and 4,969,460.

Greeninger in U.S. Pat. No. 5,324,310 describes use of both atrial and ventricular electrodes to determine a global inter-cardiac signal which thereby helps a physician verify capture manually. The Greeninger device requires a DDD pacer and two bipolar leads, wherein one lead is positioned in the atrium and the other lead is positioned in the ventricle. A physician then evaluates the global signal to determine whether capture has occurred. Markowitz in U.S. Pat. No. 5,601,615 describes a pacing device capable of verification of atrial capture by pacing in the atrium and verifying depolarization utilizing an electrode positioned in the ventricle. In order to determine ventricular capture, the '615 device paces the ventricle and then after responsive atrial activity, verifies that no wave passes an electrode positioned in the ventricle. Further, verification of capture in a single chamber pacing mode of the '615 device occurs by applying an early pacing stimulus and verifying the absence of depolarization where it would be expected after a non-disturbed cycle. The '615 device does not utilize more than one electrode in the same electrically continuous area (for example, the ventricular muscle mass or the atrial muscle mass) to verify capture of one of the electrode's stimulus. Hence, there is a need for a positive type of confirmation of capture, wherein the device is able to function in either the atria or the ventricles independently and does not require the presence of electrodes in both the atria and ventricles or conduction through the AV node between the atria and ventricles. The present invention addresses these and other needs that will become apparent from a review of the disclosure herein.

SUMMARY OF THE INVENTION

The purpose of the present invention is to provide a cardiac stimulator that utilizes at least two electrodes positioned within an electrically continuous area, for example, either one or both atria or one or both ventricles, wherein all the electrodes are utilized for pacing and at periodic times one or more electrodes verify the effectiveness of the stimulus from a predetermined electrode, thereby eliminating the need for a separate verification electrode positioned within the atria or ventricles. The present invention includes a pulse generator, at least two electrodes electrically coupled to the pulse generator, a power supply, and a microprocessor-based controller electrically coupled to the pulse generator. The microprocessor-based controller includes a means for controlling both the pulse generator and the stimulus generated by the pulse generator, means for determining intrinsic heart cycle lengths, and means for analyzing signals sensed by one or more electrodes after a pre-selected time expires after transmitting a stimulation pulse to another electrode.

In one preferred embodiment, the cardiac stimulating apparatus includes two electrodes, for example having one electrode positioned within the left ventricle and the other electrode positioned within the right ventricle. In order to determine if a stimulus transmitted at one electrode is effective, the present invention utilizes the other electrode to detect if stimulus from the first electrode induces heart muscle activity. An appropriately-timed blanking period is provided to thereby avoid detection of the stimulus transmitted at the one electrode. Stimulus from one electrode should result in a passing wave front transmitted through the electrically continuous muscle. The signal from the passing wave front is to be expected no earlier than after the depolarization conduction time of the cardiac tissue between the two electrodes. Hence a window of time can be defined following the blanking period where the second electrode should detect a depolarization signal. The capture verification testing is conducted when no intrinsic cardiac activation complex is expected to be detected at the other electrode shortly after transmission of the stimulus to the first electrode.

In another embodiment of the present invention, three electrodes are provided, wherein, without limitation, the first electrode is positioned for right ventricle pacing, a second electrode is positioned for left ventricle pacing, and the third electrode is positioned for septal pacing. In this embodiment, not only the presence of detection events, but also the relative timing of the detection events related to the passing of the wave fronts can provide information related to the effectiveness of the pacing stimulus of the electrode being tested. This is especially interesting in cases where the patient has an intrinsic heart rhythm or other condition that makes it difficult or undesirable to administer stimulation impulses continuously. Those skilled in the art will appreciate that these same principles may be applied to 3 or more electrodes positioned in a patient's atrium.

When utilizing two electrodes for verification, the relative timing of the sensing events depends on both the path the activation wave front follows and the stimulation electrodes position. Hence the relative timing of the sensing signals from the two detecting electrodes may change as the origin of the cardiac muscle activation changes. For example, if the QRS complex originates from the natural conductive system, the timing of the sensing signals from the two detecting electrodes will be different than if the QRS complex is induced by a stimulus that is applied via a right ventricular electrode. The device of the present invention further determines periodically the minimum voltage output necessary to achieve auto-capture. Automatic threshold determination may be accomplished by varying the stimulation output energy at one electrode until the other electrodes no longer detect depolarization as a result of the stimulus from the first electrode.

OBJECTS

It is accordingly a principal object of the present invention to provide a device and method for providing electrical stimulus to a patient's heart utilizing at least two electrodes positioned within an electrically continuous area of cardiac muscle wherein the electrodes may both be used for pacing, sensing, or verification of the effectiveness of the other.

Another object of the present invention is to provide a device and method of automatically verifying capture and determining the minimum threshold voltage output necessary for capture, wherein at least two electrodes are utilized and positioned within the same electrically continuous area of cardiac muscle.

A further object of the present invention is to provide a two electrode auto capture verification system incorporating a pre-defined window of time for verifying capture, after a blanking period.

These and other objects, as well as these and other features and advantages of the present invention will become readily apparent to those skilled in the art from a review of the following detailed description of the preferred embodiment in conjunction with the accompanying drawings and claims and in which like numerals in the several views refer to corresponding parts.

DETAILED DESCRIPTION

The ability to detect capture and its associated threshold capture in a pacemaker is extremely desirable since delivering pacing pulses that are ineffective may increase a patient's risks, whereas delivering pacing pulses in excess of the patient's stimulation threshold is wasteful of the pacemaker's limited power supply. In determining whether a cardiac stimulator has achieved capture, the physician or the device itself can look at electrical cardiac signals for evidence of an evoked cardiac depolarization in response to a pacing stimulus. In past cardiac stimulating devices, a single electrode has been utilized to both pace and verify capture of this electrode stimulus. Problems arise using this method including blind spots due to after potentials, tissue polarization and high stimulating voltage spikes.

In monosite cardiac pacing, where there is one stimulation site per part of the heart that is electrically continuous, the resulting depolarization is by definition traveling away from the stimulating electrode so there is no depolarization wave front passing the electrode. Passing wave fronts have characteristics that are readily detected by standard sensing circuits. When the depolarization wave front is traveling away from the electrode, the sensing circuit has to detect depolarization through other signal characteristics (i.e., from depolarization after potentials or from a resulting T-wave characteristics). These signal characteristics are less ideal, are of lower frequencies and may be disturbed by the stimulation artifact and its after potential.

In multisite cardiac pacing, where there is more than one stimulation site per part of the heart that is electrically continuous, there is additional information available for detection of a depolarization wavefront that is caused by stimulating a given electrode. A second electrode situated elsewhere in the same electrically continuous portion of the heart is utilized to detect depolarization induced by the first electrode, wherein the depolarization wavefront propagates through the muscle tissue and passes the second electrode sometime after the stimulation impulse. The passing of the depolarization wavefront causes a signal which has the characteristic of a "normal" sensing signal as it is known from the detection of intrinsic cardiac activity in monosite cardiac pacing. Sensing technology and circuitry of known construction can be used for detection of the depolarization. Stimulation artifact and its resulting after potentials are ignored by including in this sensing circuit a timed blanking period and a window of time in which the depolarization wave front is detected by the second electrode. The fact that the passing wave front will not reach the second electrode earlier than after the depolarization conduction time of the cardiac tissue between the two electrodes allows for an appropriate blanking period, without compromising the ability to detect the passing wave front.

The electrodes of the present invention may be utilized in conjunction with stimulating the heart's ventricles either simultaneously or sequentially. Such a system is useful in treating patients with congestive heart failure (CHF). Typically a cardiac stimulator utilized in CHF patients is programmed to stimulate continuously. During special capture verifications sequences occurring at selected intervals (i.e., once per day, once per hour, once every tenth heart beat) the function of the electrodes switches to a verification state rather than a stimulating function.

The auto capture sequence is controlled by the microprocessor based controller coupled to the pulse generator. An appropriately timed blanking period is of a very short duration, on the order of 10 milliseconds, and prevents a detecting electrode from detecting the actual stimulus transmitted to the testing electrode. During this blanking period, the designated detection electrodes are inactive. In a configuration with one or more detecting electrodes, after the preset blanking period, the detection window starts. This window should be long enough to cover the longest possible activation conduction time between the electrodes. Without any limitation intended, the time of the detection window could range from 50–350 milliseconds.

The window of time may further be narrowed by storing in the memory of the microprocessor based controller the amount of time between the test stimulus and the actual detection of capture for the electrodes, over one or several verifications. The data may then be averaged and utilized in later cycles to define the window of time (to be slightly greater than the average time taken between stimulus and detection) during capture verification, which enables the test stimulus to be applied as late as possible and thereby minimally interfere with the heart rhythm.

When two or more detecting electrodes are present, the microprocessor based controller can also be programmed to check for changes in the relative timing of the sensing events of the multiple sensing electrodes. This may be accomplished by storing the time at which each electrode experiences a sensing event relative to another electrode, or relative to a mean of the moments of sensing on all detecting electrodes, associated with the same cardiac cycle. This set of relative timings is defined to be the reference sensing pattern, which is stored for comparison with the pattern found in a later cycle. Then, in a pacing cycle in which the test stimulus is administered, the sensing pattern is collected again and compared with the stored reference sensing pattern. If one or more of the detecting electrodes' relative sensing timings are off more than a pre-determined amount, a change in the relative sensing timing pattern could be declared and the test stimulus be declared to have captured the heart. Having generally described the present invention, focus of the description will next be directed to the figures.

Figure 1:
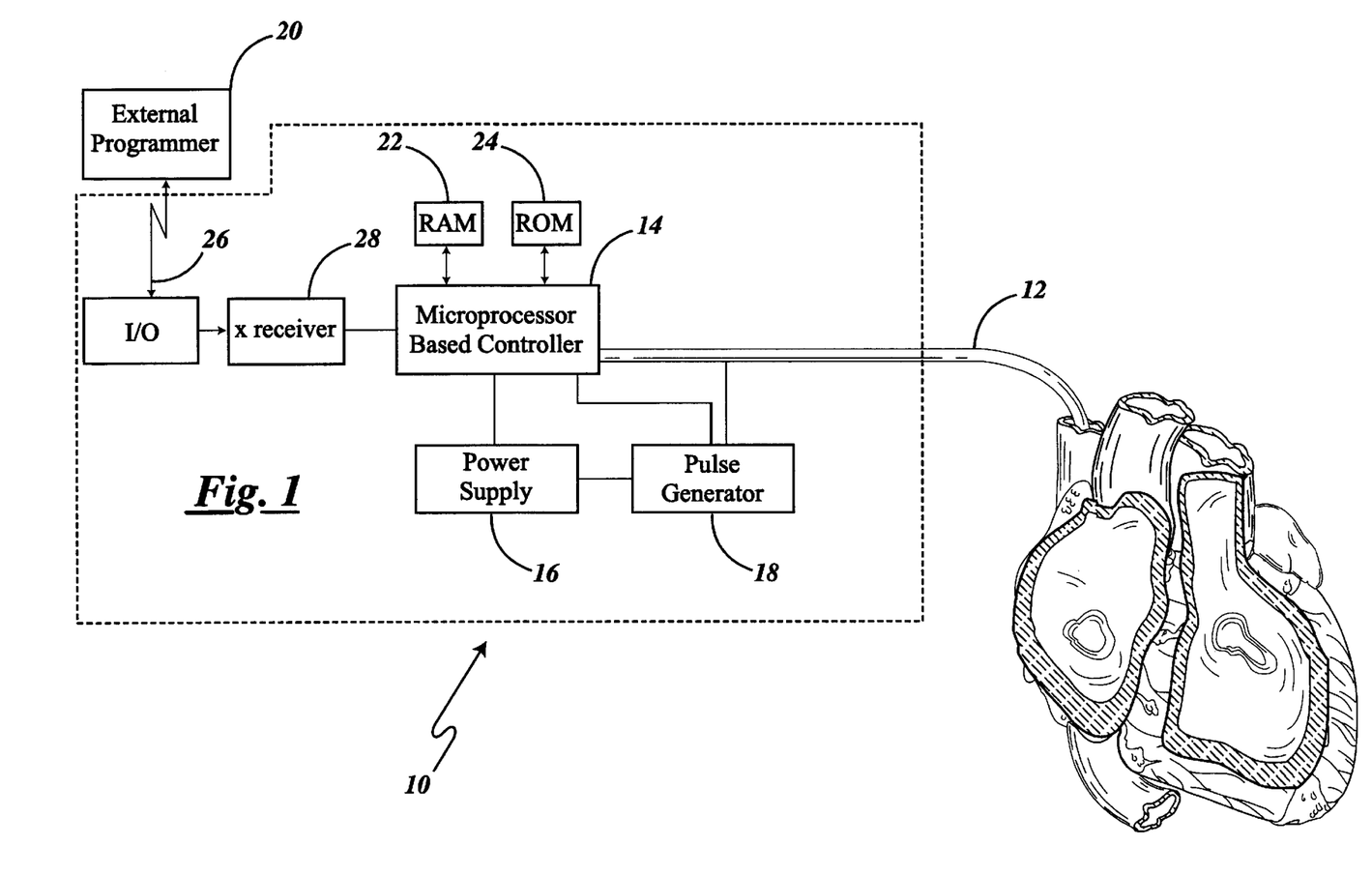
FIG. 1 is a partial sectional perspective view of a patient's heart having a distal end of a lead inserted into the patient's heart and a proximal end of the lead connected to a cardiac stimulator shown in block diagram.

Referring first to FIG. 1, the cardiac stimulator, designated generally by numeral 10, is shown having lead 12 inserted into a patient's heart. The cardiac stimulator 10 generally includes a microprocessor based controller 14, a power supply 16, a pulse generator 18, and an external programmer 20. The first or distal end of the pacing lead 12 is inserted into the patient's heart and the second or proximal end of the lead is electrically connected generally to the cardiac stimulator 10, and specifically to the pulse generator 18 and micro processor based controller 14. Those skilled in the art will appreciate that the lead 12 may be of a suitable construction including one or more electrodes. Further sense amplifiers of known construction may be incorporated internally within the micro processor based controller circuitry.

The micro processor based controller 14 is programmed to operate in any one of a plurality of pacing modes in a manner known to those skilled in the art, including AV-sequential pacing. The micro processor 14 further has both RAM (random access memory) 22 and ROM (read only memory) 24 for storing programs and data which generally allows the following: the processing of signals from electrogram, controlling the automatic capture verification sequence, controlling the automatic threshold adjustment sequence, storing various information derived from the automatic capture sequence, and changing the preset constants of the program. The microprocessor 14 controls the cardiac stimulating pulses delivered by pulse generator 18 to two or more stimulating electrodes (not shown). A cardiac stimulating device 10 capable of telemetering various status information including selecting a pacing mode and other parameters is commercially available from for example, Cardiac Pacemakers, Inc., St. Paul, Minn. the details of which are incorporated herein by reference. The external programmer 20 having a micro processor and associated memory transmits information in a conventional way through a telemetry link 26 and transmission receiver 28 of the cardiac stimulators micro processor 14. Using the external programmer 20 and the telemetry link 26, operating parameter values for the cardiac stimulator 10 can be delivered to it by an operator for setting the cardiac cycle pacing parameter values to be utilized and other various features of the stimulator 10.

Figure 2:
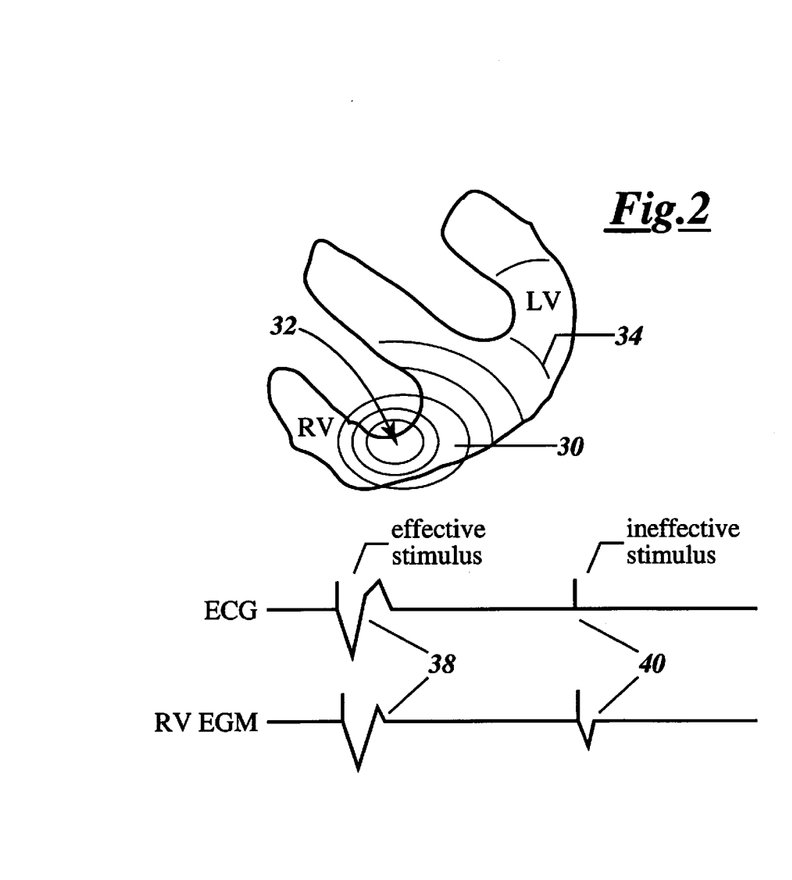
FIG. 2 is a block view of the ventricular portion of a patient's heart being sensed and paced in the right ventricle and shown in conjunction with ECG (surface electrocardiogram) and EGM (intra cardiac electrogram) plots, wherein a pacing signal propagates from the right ventricle.
Figure 3:
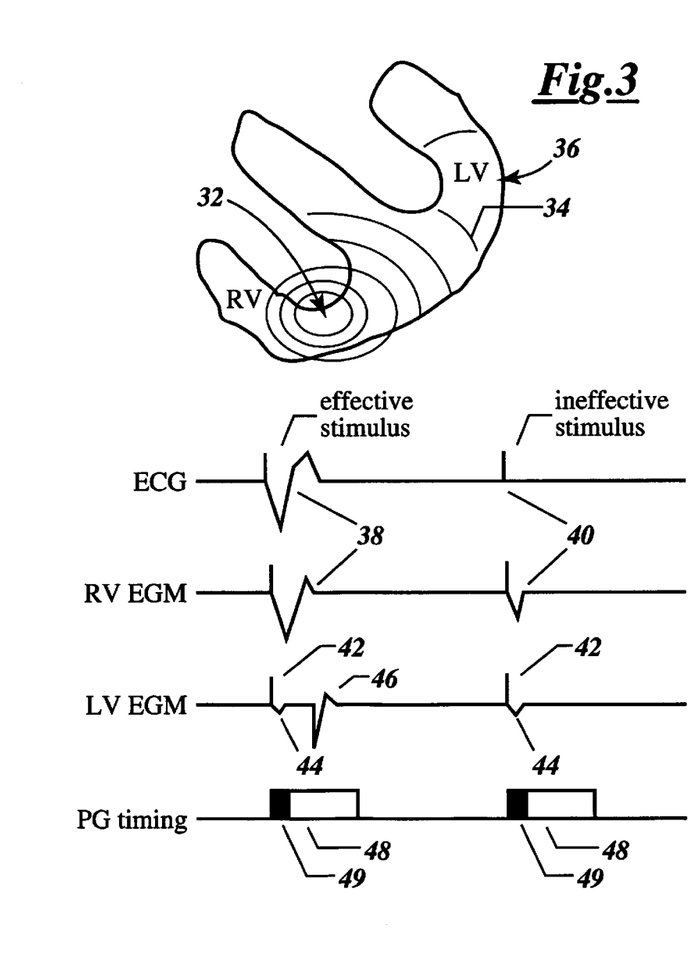
FIG. 3 is a block view of the ventricular portion of a patient's heart being paced in the right ventricle and shown in conjunction with ECG and EGM plots, wherein a paced activation propagates from the right ventricle.

FIG. 2 shows a typical waveform 34 propagating through the ventricular muscle mass, wherein the stimulating electrode 32 is positioned within the right ventricle 30. A graphic comparison of an ECG signal and a right ventricular electrogram is also shown. An ECG and RV EGM wave patterns 38 associated with an effective stimulus and wave patterns 40 associated with an ineffective stimulus are represented graphically. FIG. 3 further shows an additional electrode 36 within the left ventricle and positioned for detecting the depolarization wave form 34. The ECG and RV (right ventricular) EGM and LV (left ventricular) EGM are graphically shown for comparison. The LV EGM from the left ventricular electrode 36 shows distinct pacing spikes 42, artifact 44 and depolarization 46. The information from the LV EGM and RV EGM can readily be analyzed correctly utilizing an appropriate blanking period 49 and window 48 for detection of depolarization (see FIG. 3). When effective stimulation via the RV electrode occurs, the depolarization 46 is sensed off the left ventricular EGM at a time within the detection window 49.

Figure 4:
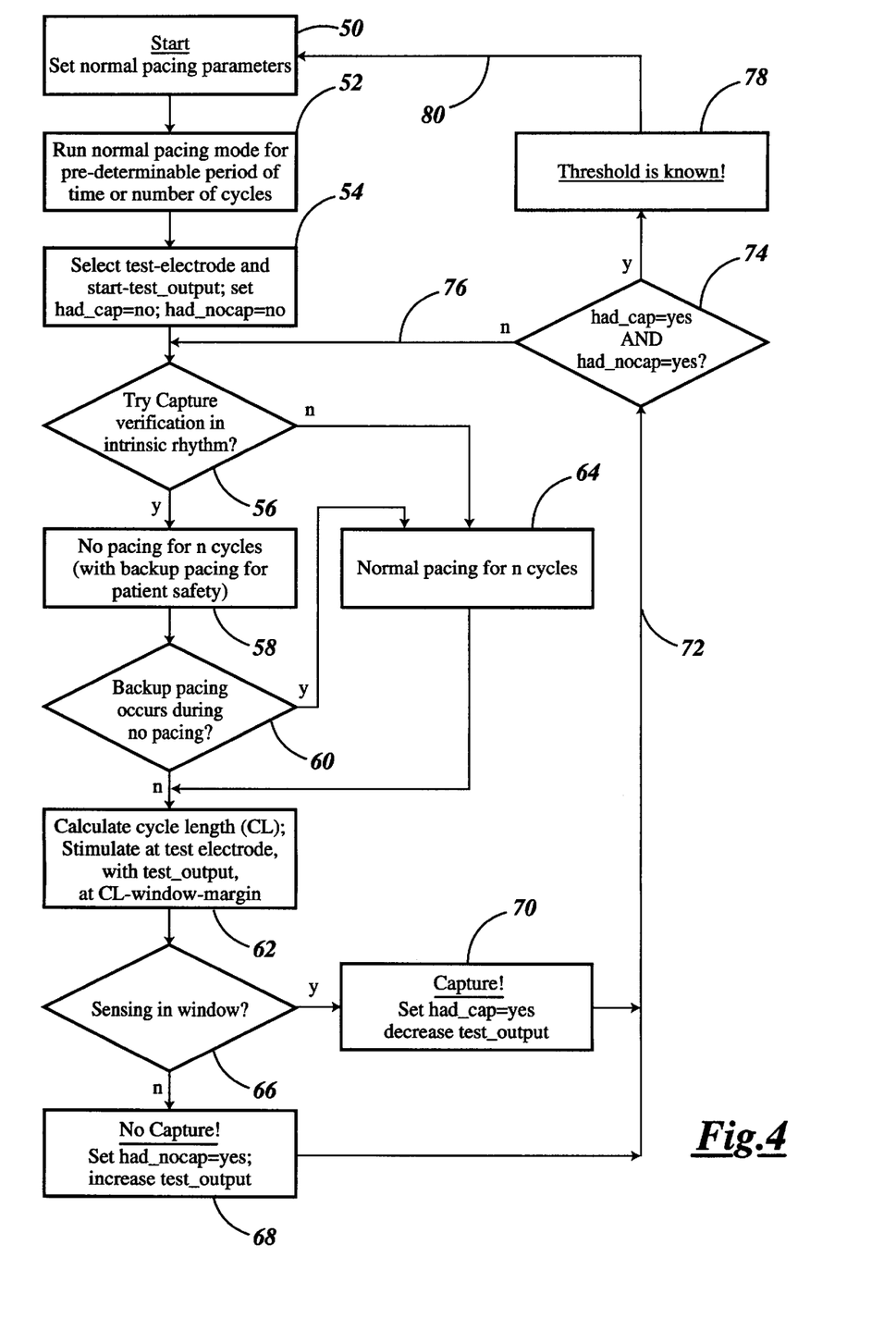
FIG. 4 is a flow diagram of an algorithm used to determine capture and threshold in a two electrode system of the present invention.

FIG. 4 shows an algorithm suitable for use in conjunction with the present invention. Of course, the algorithm is not intended to be limiting, but rather describes a preferred algorithm for verifying the threshold and capture utilizing two electrodes positioned within an electrically continuous area of cardiac muscle. The user first sets the normal pacing parameters (see block 50) and normal pacing occurs for a predetermined number of cardiac cycles (see block 52). The capture verification test then begins, testing an electrode previously selected as the test electrode (see block 54). If capture verification is to be tested during an intrinsic rhythm, then pacing is delayed for n predetermined cycles (see decision block 56 and block 58). If capture verification is not to be tested during intrinsic rhythm, pacing continues during the predetermined n cycles (see block 64). If backup pacing occurs during the delayed pacing, then normal pacing begins for n cycles. At the end of n cycles the microprocessor based controller 14 calculates the cycle length and then stimulates the test electrode, utilizing the other electrode as a detector, at a point in time that is [the calculated cycle length, minus the duration of the detection window, minus a predeterminable margin] after the event that defines the end of the previous cardiac cycle (see decision block 60 and block 62). If a depolarization is sensed by the detection electrode (see decision block 66) then capture is verified (block 70) and the test output is decreased a predetermined amount. If a depolarization is not sensed, then the test output voltage is increased (see block 68). Once the test output is either increased or decreased then capture is re-verified as at loop 72. If prior to the verification there was capture and then upon re-verification there was no capture, or vice versa (see decision block 74), then the threshold output is known (block 78) and then the pacing returns to its normal pacing parameters (loop 80). If the upon re-verification there was capture where there was capture before, or no capture where there was no capture before, then capture verification continues (see loop 76) until the threshold is determined (block 78).

Figure 5:
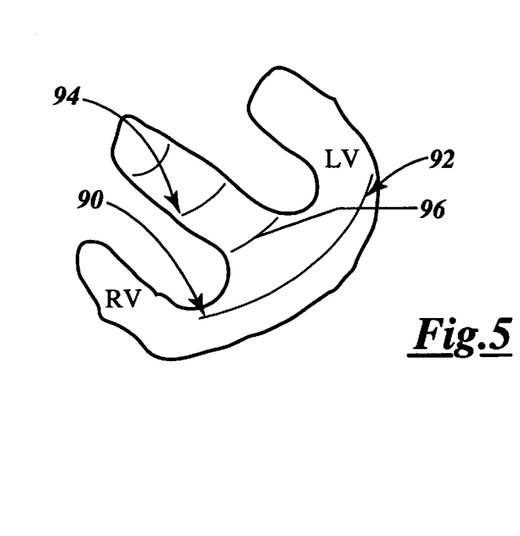
FIG. 5 is a block view of the ventricular portion of a patient's heart having pacing electrodes positioned in the right ventricle, left ventricle and near the septum, and further showing the propagation of an intrinsic activation.
Figure 6:
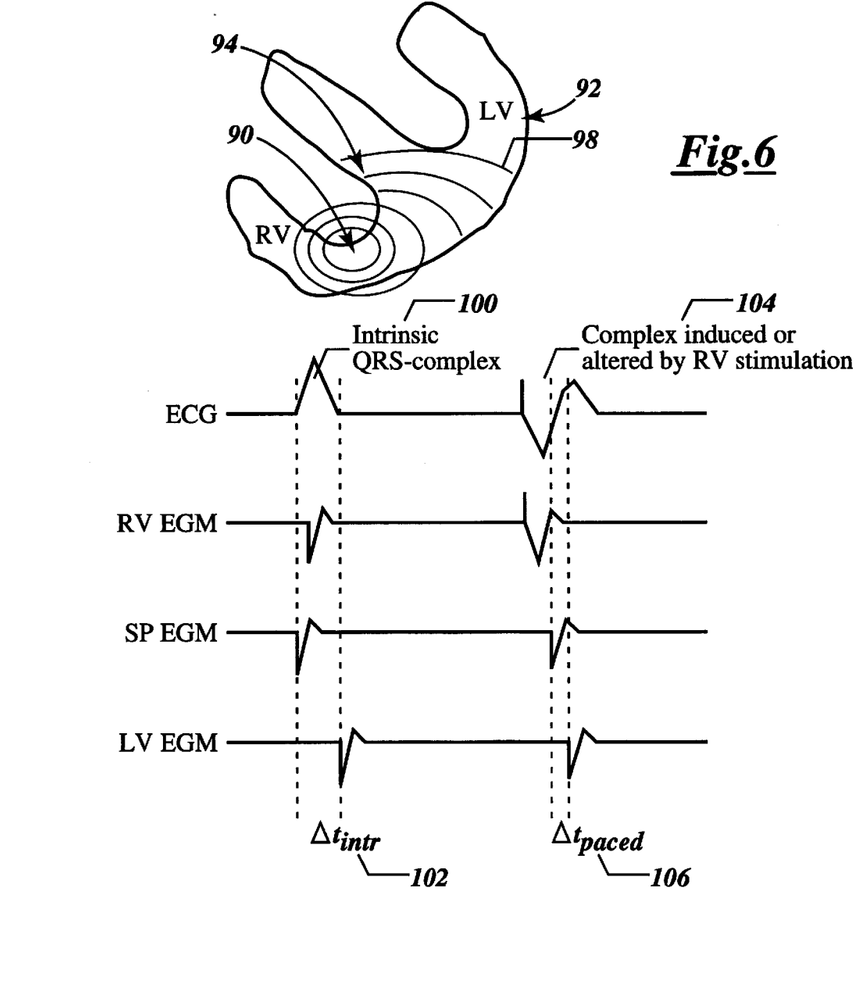
FIG. 6 is a block view of the ventricular portion of a patient's heart being paced in the right ventricle and shown in conjunction with ECG and EGM plots, wherein a paced activation propagates from the right ventricle.

FIG. 5 shows the positioning of RV electrode 90, septal electrode 94 and LV electrode 92 together with the depolarization waveform 96 of an intrinsic activation. FIG. 6 shows the depolarization waveform 98 wherein RV electrode 90 is being tested or stimulated. FIG. 6 also illustrates graphically the ECG, RV EGM, LV EGM and Septal (SP) EGM for intrinsic 100 and induced 104 activation, where the RV electrode is used as the test electrode. As the activation originates from different locations and thus follows different paths in the two situations, the time (Δt) between the detection of the wavefront via the detecting SP and LV electrodes (the time $t_{SP}$ of detecting via one detecting electrode, relative to the time $t_{LV}$ of detecting via the other detecting electrode) is different. Note that the time of detection of each electrode could also be related to a mean of times of detection of all detecting electrodes, instead of directly to that of one other as illustrated in FIG. 6 (not shown). In a multiple detecting electrode configuration, the time between detections could change between any combination of two electrodes, or could change for each electrode compared with the mean. In the latter case, each electrode would have its own "Δt".

Figure 7:
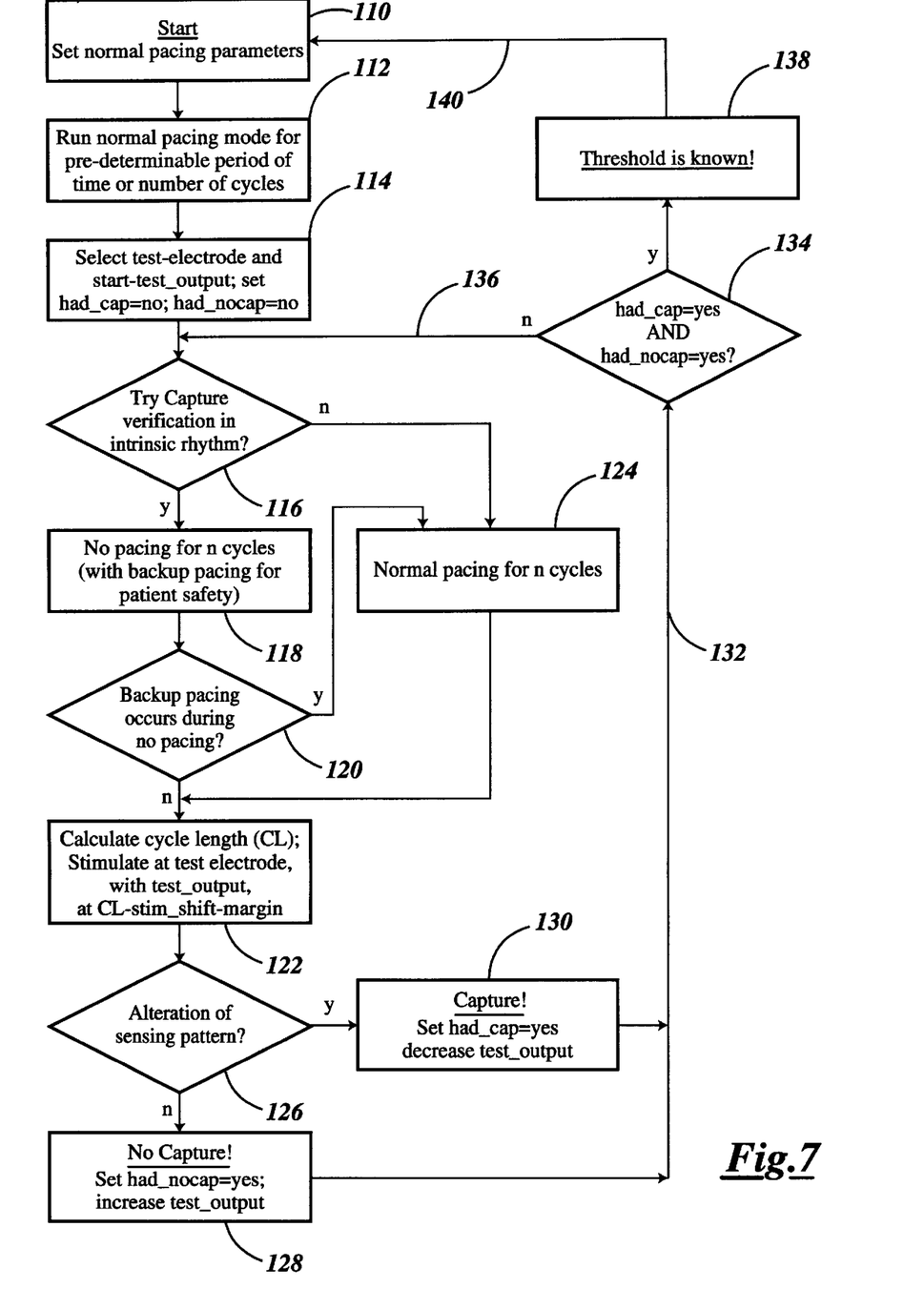
FIG. 7 is a flow diagram of an algorithm used to determine capture and threshold in a three electrode system of the present invention.

FIG. 7 shows an algorithm suitable for use in conjunction with a three electrode pacing system of the present invention within an electrically continuous area of cardiac muscle. The user first sets the normal pacing parameters (see block 110) and normal pacing occurs for a predetermined number of cardiac cycles (see block 112). The capture verification test then begins, testing an electrode previously selected as the test electrode (see block 114). If capture verification is to be tested during an intrinsic rhythm, then pacing is delayed for n predetermined cycles (see decision block 116 and block 118). If capture verification is not to be tested during intrinsic rhythm, pacing continues during the predetermined n cycles (see block 124). If backup pacing occurs during the delayed pacing, then normal pacing begins for n cycles (see decision block 120). At the end of n cycles the microprocessor based controller 14 calculates the cycle length and then stimulates the test electrode, utilizing the other electrodes as detectors, at a point in time equalling [the calculated cycle length minus the time required in order to allow for detection of a change in sensing pattern, minus a pre-determinable margin] after the event that defines the end of the previous cardiac cycle (see decision block 120 and block 122). If the sensing pattern, as seen during the n cycles, is different during the test cycle (see decision block 126), then capture is verified (block 130) and the test output is decreased a predetermined amount. If a depolarization is detected (see decision block 126) then capture is verified (block 130) and the test output is decreased a predetermined amount. If a depolarization is not detected, then the test output is increased (see block 128). Once the test output is either increased or decreased then capture is re-verified as at loop 132. If prior to the verification there was capture and then upon re-verification there was no capture, or vice versa, (see decision block 134), then the threshold output is known (block 138) and then the pacing returns to its normal pacing parameters (loop 140). If upon re-verification, there was capture where there was capture before, or no capture where there was no capture before, then capture verification continues (see loop 136) until the threshold is determined (block 138).

This invention has been described herein in considerable detail in order to comply with the patent statutes and to provide those skilled in the art with the information needed to apply the novel principles and to construct and use such specialized components as are required. However, it is to be understood that the invention can be carried out by specifically different devices, and that various modifications, both as to the equipment details and operating procedures, can be accomplished without departing from the scope of the invention itself.

What is claimed is:

1. A method for verifying capture of a stimulation pulse delivered to a pre-selected chamber of a patient's heart, by a cardiac rhythm management device of the type having means for sensing cardiac electrogram signals, a programmable controller coupled to receive the sensed electrogram signals, and stimulation means controlled by the controller for applying cardiac stimulation pulses to a patient's heart in response to control signals from the controller in accordance with predetermined parameters, wherein the stimulation pulse is delivered to the preselected chamber on a demand or continuous basis, said method comprising the steps of:

(a) positioning at least three electrodes in at least one of an electrically continuous area of the heart's atriums and an electrically continuous area of the heart's ventricles;

(b) setting predetermined parameters of the cardiac rhythm management device;

(c) delivering stimulation pulses in accordance with the predetermined parameters;

(d) transmitting from the cardiac rhythm management device a test stimulation pulse having a predetermined output energy to a predetermined first electrode; and (e) sensing for a depolarization waveform at at least two of the other electrodes, wherein a sensed depolarization indicates capture.

2. The method as recited in claim 1, further including the steps of:

i) during delivery of stimulation pulses in accordance with the predetermined parameters, storing in memory of the programmable controller a first time relation between a depolarization detection on at least two of the other electrodes;

ii) after transmitting said test stimulation pulse, storing in memory of the programmable controller a second time relation between a second depolarization detection on at least two of the other electrodes; then iii) comparing said stored first and second timing relations wherein a difference between the first and second relation that exceed a predetermined amount indicates a change in an effectiveness of the stimulation pulses.

3. The method as recited in claim 2, wherein the steps of storing the first and second timing relations further includes the step of determining the first and second time relation from a set of relative times, calculated for each of the detecting electrodes, with respect to a time between the depolarization detection on at least two of the other electrodes over the same cardiac cycle.

4. The method as recited in claim 1, wherein the step of transmitting the test stimulation pulse further includes calculating an appropriate time for delivering the test stimulation pulse, said appropriate time being dependant upon a cardiac cycle length, and wherein the test stimulation pulse is transmitted with sufficient time to detect depolarization.

5. The method as recited in claim 1, further including the step of reducing the output energy and repeating steps c–e if a depolarization is sensed at least two of the other electrodes.

6. The method as recited in claim 1, and further including the step of identifying a smallest output energy wherein a depolarization waveform is sensed, thereby reducing unnecessary power drain of a power supply of the cardiac rhythm management device.

7. A method for verifying capture of a stimulation pulse delivered to a pre-selected chamber of a patient's heart, by a cardiac rhythm management device of the type having means for sensing cardiac electrogram signals, a programmable controller coupled to receive the sensed electrogram signals, and stimulation means controlled by the controller for applying cardiac stimulation pulses to a patient's heart in response to control signals from the controller in accordance with predetermined parameters, wherein the stimulation pulse is delivered to the preselected chamber on a demand or continuous basis, said method comprising the steps of:

(a) positioning a plurality of electrodes in at least one of an electrically continuous area of a heart's atriums and an electrically continuous area of the heart's ventricles;

(b) setting predetermined parameters of the cardiac rhythm management device;

(c) delivering stimulation pulses in accordance with the predetermined parameters;

(d) transmitting from the cardiac rhythm management device a test stimulation pulse having a predetermined output energy to a predetermined electrode; and (e) sensing for a depolarization waveform at predetermined electrodes, wherein a sensed depolarization indicates capture.

8. The method as recited in claim 7, further including the steps of:

(i) during delivery of stimulation pulses in accordance with the predetermined parameters, storing in memory of the programmable controller a first time relation between sensing a first depolarization waveform on at least two electrodes;

(ii) after transmitting said test stimulation pulse, storing in memory of the controller a second time relation between sensing a second depolarization waveform on at least two electrodes;

(iii) comparing said first and second timing relations wherein a difference between the first and second timing relations indicates a change in an effectiveness of the stimulation pulses.

9. The method as recited in claim 8, wherein the steps of storing the first and second timing relations further includes the step of determining the first and second time relation from a set of relative times, calculated for each of the detecting electrodes, with respect to a time between the depolarization detection on at least two electrodes over the same cardiac cycle.

10. The methods as recited in claim 7, wherein the step of transmitting the test stimulation pulse further includes calculating an appropriate time for delivering the test stimulation pulse, said appropriate time being dependant upon a cardiac cycle length, and wherein the test stimulation pulse is transmitted with sufficient time to detect depolarization.

11. The method as recited in claim 7, and further including the step of identifying a smallest output energy wherein a depolarization waveform is sensed, thereby reducing unnecessary power drain of a power supply of the cardiac rhythm management device.

* * * * *